United States Patent [19]

Leppard et al.

[11] Patent Number: 4,558,131

[45] Date of Patent: Dec. 10, 1985

[54] COLOR-PHOTOGRAPHIC RECORDING MATERIAL

[75] Inventors: David G. Leppard, Marly; Jean Rody, Riehen, both of Switzerland

[73] Assignee: Ciba-Geigy AG, Basel, Switzerland

[21] Appl. No.: 562,188

[22] Filed: Dec. 15, 1983

[30] Foreign Application Priority Data

Dec. 16, 1982 [CH] Switzerland ................. 7316/82

[51] Int. Cl.$^4$ ........................................... C07D 211/50
[52] U.S. Cl. ................................. 546/222; 430/551; 546/224; 546/241
[58] Field of Search ................... 546/222, 224, 241

[56] References Cited

U.S. PATENT DOCUMENTS

| 4,148,784 | 4/1979 | Malherbe | 546/222 |
| 4,197,236 | 4/1980 | Rosenberger | 546/222 |
| 4,340,533 | 7/1982 | Rody | 546/222 |
| 4,344,877 | 8/1982 | Nikles | 546/222 |

*Primary Examiner*—Paul R. Michl
*Attorney, Agent, or Firm*—Wenderoth, Lind & Ponack

[57] ABSTRACT

Compounds which contain in their molecule both a hydroquinone monoether or resorcinol monoether radical and a polyalkylpiperidine radical are effective stabilizers for photographic dyes and their intermediates. In particular, they act as stabilizers against damage by light.

4 Claims, No Drawings

COLOR-PHOTOGRAPHIC RECORDING MATERIAL

The present invention relates to a colour-photographic recording material which contains in at least one photo-sensitive silver halide emulsion layer and/or in at least one of the conventional auxiliary layers, at least one specific polyalkylpiperidine compound as a stabiliser.

Polyalkylpiperidines are sterically hindered amines which are generally known as light stabilisers for organic materials, in particular for polymers. German Offenlegungsschrift No. 2,126,954 has also already proposed using polyalkylpiperidines as agents against the fading of colour photographs. European Pat. No. A 11,051 has furthermore proposed using certain polyalkylpiperidine derivatives containing at least one phenol group as light stabilisers for colour photographs. These compounds are polyalkylpiperidine esters of hydroxybenzylmalonic acids.

In continuation of this research work, it has been found that compounds which contain both a sterically hindered hydroquinone or resorcinol monoether radical and a polyalkylpiperidine radical have a surprisingly improved action.

The present invention thus relates to a colour-photographic recording material which contains, in at least one photosensitive silver halide emulsion layer, an interlayer, an image-receiving layer and/or a protective layer, at least one compound, as a stabiliser, which contains in its molecule at least one hydroquinone monoether or resorcinol monoether radical, the free OH groups of which are sterically hindered, and at least one polyalkylpiperidine radical.

These stabilisers are, in particular, compounds of the formula I $$[A]_a Z—B]_b \qquad (I)$$

in which a and b independently of one another are integers from 1 to 5 and (a+b) is a number from 2 to 6, A is a monovalent hydroquinone monoether or resorcinol monoether radical, the free OH group of which is sterically hindered, Z is an (a+b)-valent organic radical linking groups A and B and B is a monovalent polyalkylpiperidine radical of the formula II or III

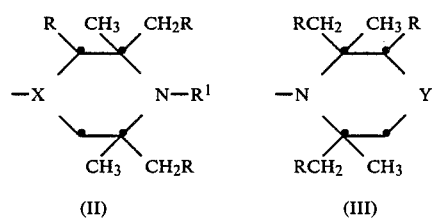

in which R is hydrogen or methyl, X is a group

or a 5-membered or 6-membered heterocyclic spiro ring with two O or N atoms, Y is a group —CH$_2$— or —CH(R$^2$)— or a 5-membered or 6-membered heterocyclic spiro ring with two O or N atoms, R$^1$ is hydroxyl, C$_1$–C$_{12}$-alkyl, C$_3$–C$_6$-alkenyl, C$_3$–C$_4$-alkynyl, C$_7$–C$_{12}$-phenylalkyl, glycidyl, C$_1$–C$_4$-alkyl which is substituted by halogen, —CN, —COOR$^3$ or —CON(R$^4$)(R$^5$), a group —CO—R$^6$, —CO—OR$^3$, —CO—N(R$^4$)(R$^5$), —CH$_2$—CH(R$^7$)—OR$^8$, —SO—R$^9$, —SO$_2$—R$^9$, —OR$^3$ or —OOC—R$^6$, or a group —Z°—A, in which Z° is a divalent organic radical, and, if b is 1, R$^1$ can also be a group of the formula

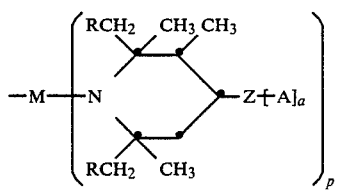

in which p is 1, 2 or 3 and, if p is 1, M is a divalent group and is C$_2$–C$_{12}$-alkylene, C$_4$–C$_8$-alkenylene, xylylene or a radical of the formula —CH$_2$—C≡C—CH$_2$—,

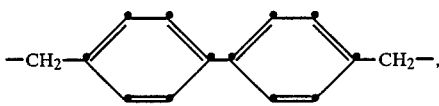

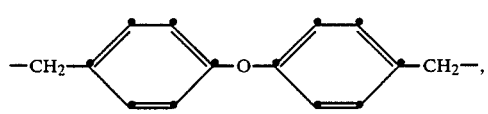

—CH$_2$—COO—R$^{10}$—OOC—CH$_2$—, —CH$_2$—CH(OH)—CH$_2$—, —CH$_2$CH(OH)CH$_2$—D—CH$_2$CH(OH)CH$_2$—, —CH$_2$—CH(R$^7$)—OOC—R$^{11}$—COO—CH(R$^7$)—CH$_2$— or —CO—NH—G—NH—CO—, in which D is a divalent radical of the formula —O—R$^{12}$—O— or —OOC—R$^{11}$—COO— and G is a divalent aliphatic, cycloaliphatic, aromatic or aromatic-aliphatic radical having 6–15 C atoms, or, if p is 2, M is a trivalent radical of the formula T—CH$_2$CH(OH)CH$_2$]$_3$ or
R$^{13}$[COO—CH(R$^7$)—CH$_2$]$_3$ in which T is a trivalent radical of the formula

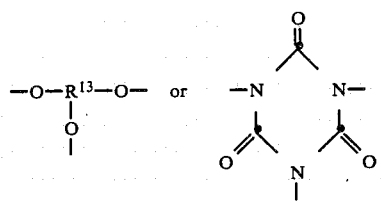

or, if p is 3, M is a quadrivalent radical of the formula

Q—CH₂CH(OH)CH₂]₄ or
R¹⁴—COO—CH(R⁷)—CH₂]₄ in which Q is a group of the formula

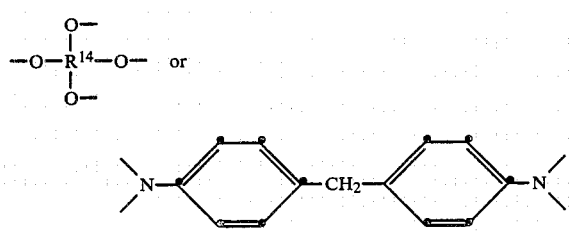

$R^2$ is hydroxyl, —OR¹⁵, —OOC—R⁶, —OOC—N(R⁴)(R⁵), —N(R¹⁶)—CO—R⁶ or —N(R¹⁶)—CO—N(R⁴)(R⁵), or is a group —Z°—A, and, if b is 1, $R^2$ can also be a group of the formula

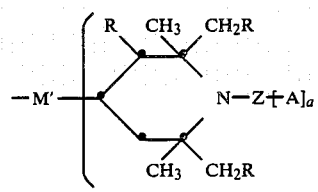

in which r is 1, 2 or 3 and, if r is 1, M' is a divalent group of the formula —OOC—R¹¹—COO—, —OOC—NH—G—NH—COO—, —N(R¹⁶)—CO—R¹¹—CO—N(R¹⁶)— or —N(R¹⁷)—R¹⁸—N(R¹⁷)—, or, if r is 2, M' is a trivalent group of the formula R¹⁹[COO]₃ or R¹⁹[CON(R¹⁶)]₃ or, if r is 3, M' is a quadrivalent group of the formula

R²⁰[COO]₄ or R²⁰[CON(R¹⁶)]₃

$R^3$ is C₁–C₁₂-alkyl, benzyl or cyclohexyl, $R^4$ is C₁–C₁₂-alkyl, allyl, cyclohexyl, benzyl or phenyl and $R^5$ is hydrogen, C₁–C₈-alkyl or allyl, or $R^4$ and $R^5$, together with the N atom, are a 5-membered or 6-membered heterocyclic ring, $R^6$ is hydrogen, C₁–C₁₂-alkyl, C₂–C₆-alkenyl, chloromethyl, C₅–C₁₂-cycloalkyl, C₇–C₁₂-phenylalkyl, phenyl, C₇–C₁₀-alkylphenyl, or phenyl, phenylmethyl or phenethyl which is substituted by 1 or 2 C₁–C₄-alkyl groups and a hydroxyl group, $R^7$ is hydrogen, C₁–C₄-alkyl, C₂–C₁₃-alkoxymethyl, phenyl or phenoxymethyl, $R^8$ is hydrogen, C₁–C₁₂-alkyl, —CO—R⁶ or —CO—N(R⁴)(R⁵), $R^9$ is C₁–C₁₂-alkyl, phenyl or C₇–C₂₂-alkylaryl, $R^{10}$ is C₂–C₁₂-alkylene, C₄–C₈-oxaalkylene or cyclohexylene, $R^{11}$ is a direct bond, C₁–C₁₂-alkylene, C₂–C₆-alkenylene, C₆–C₁₂-cycloalkylene or -cycloalkenylene or C₆–C₁₂-arylene, $R^{12}$ is C₂–C₁₂-alkylene, C₆–C₁₂-cycloalkylene, C₆–C₁₂-arylene or phenylene-W-phenylene- and W is —O—, —CH₂—, >C(CH₃)₂ or —SO₂—, $R^{13}$ is a trivalent aliphatic hydrocarbon radical having 3–10 carbon atoms or a trivalent aromatic hydrocarbon radical having 6–10 C atoms, $R^{14}$ is a quadrivalent aliphatic hydrocarbon radical having 4–10 C atoms or a quadrivalent aromatic hydrocarbon radical having 6–12 C atoms, $R^{15}$ is hydrogen, C₁–C₁₂-alkyl, allyl or benzyl, $R^{16}$ is hydrogen, C₁–C₁₂-alkyl, C₅–C₁₂-cycloalkyl or benzyl, $R^{17}$ is hydrogen, C₁–C₁₂-alkyl, allyl, benzyl, C₂–C₁₂-alkanoyl or benzoyl, $R^{18}$ is C₂–C₁₂-alkylene, C₄–C₁₆-alkylene which is interrupted by one or more —O— or —N(R¹⁶)—, or C₆–C₁₂-cycloalkylene, $R^{19}$ is a trivalent aliphatic radical having 3–10 C atoms, a trivalent aromatic radical having 6–10 C atoms or the group N(CH₂)₃ and $R^{20}$ is a quadrivalent aliphatic radical having 4–10 C atoms or a quadrivalent aromatic radical having 6–12 C atoms.

The group Z can be bonded to the radical A via the ether groups thereof or directly to the benzene ring of A. Z is bonded to B either at the N atom of the piperidine ring, as expressed in formula III, or in the 4-position of the piperidine ring or at a heterocyclic spiro ring in the 4-position, as expressed by formula II. Depending on the value of a and b, Z is a 2- to 6-valent organic radical. As well as hydrocarbon radicals, this can also contain O, N, S or P. It preferably contains ester or amide groups, but can also contain heterocyclic radicals, for example an s-triazine radical or a hydantoin radical. Z is generally chosen according to its accessibility by synthesis and its suitability for permanent bonding of the groups A and B. The influence of Z on the stabilising activity of the compounds of the formula I is generally low, whilst A and B are the actual effective groups.

The polyalkylpiperidine groups B are the same as those known in light stabilisers for plastics and varnishes. The groups B can be represented by formula II or III, depending on the bonding to Z. A heterocyclic spiro ring X or Y in these formulae can be, for example, a 2-spiro-1,3-dioxolane, 2-spiro-1,3-dioxane, 4-spiroimidazoline-2,5-dione, 2-spirooxazolidin-4-one or 5-spirooxazolidin-4-one. A group of the formula II can be, for example, a group of the formula

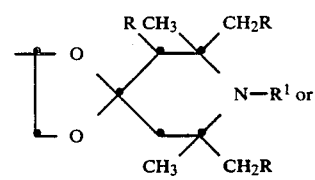

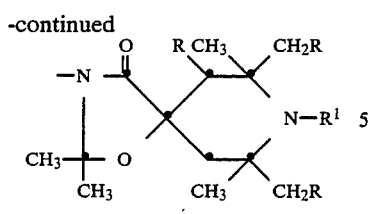

A group of the formula III can be, for example, a group of the formula

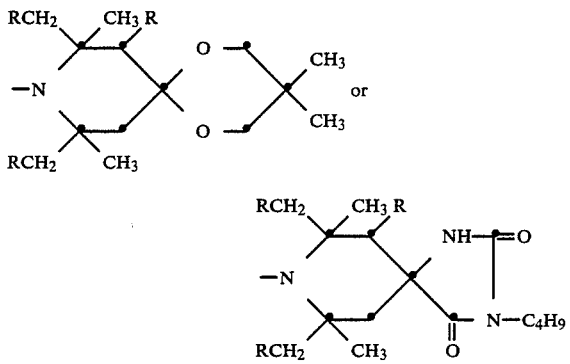

A $C_1$–$C_4$-alkyl group $R^7$ can be, for example, methyl, ethyl, n-propyl, isopropyl, n-butyl, isobutyl or tert.-butyl.

$C_1$–$C_8$-Alkyl $R^5$ can moreover also be, for example, isoamyl, n-hexyl, 2-ethylbutyl, n-octyl or 2-ethylhexyl. $C_1$–$C_{12}$-Alkyl $R^1$, $R^3$, $R^4$, $R^6$, $R^8$, $R^9$, $R^{15}$, $R^{16}$ or $R^{17}$ can furthermore also be, for example, n-decyl, isononyl or n-dodecyl. $C_2$–$C_{15}$-Alkoxymethyl $R^7$ can be, for example, methoxy-, ethoxy-, butoxy-, hexyloxy-, octyloxy- or dodecyloxy-methyl.

$C_3$–$C_6$-Alkenyl $R^1$ can be, in particular, alkenylmethyl, for example allyl, methallyl, 2-but-1-enyl or 3,3-dimethylallyl. $C_2$–$C_6$-Alkenyl $R^6$ can be, for example, vinyl, 2-propenyl, allyl, 2-methylvinyl, 2,2-dimethylvinyl or methallyl. $C_3$–$C_4$-Alkynyl $R^1$ can be, for example, propargyl or 3-methylpropargyl.

Alkyl $R^1$ which is substituted by halogen, —CN, —COOR$^3$ or —CON(R$^4$)(R$^5$) can be, for example, chloromethyl, 2-chloropropyl, cyanomethyl, 2-cyanoethyl, ethoxycarbonylmethyl, octyloxycarbonylmethyl, 2-methoxy-, 2-isopropoxy- or 2-hexyloxy-carbonylethyl, N-dimethylcarbamoylmethyl, N-diallylcarbamoylethyl or 2-(morpholinocarbonyl)-ethyl.

$C_5$–$C_{12}$-Cycloalkyl $R^6$ or $R^{16}$ can be, for example, cyclopentyl, methylcyclopentyl, cyclohexyl, dimethylcyclohexyl, cyclooctyl or cyclododecyl.

$C_7$–$C_{12}$-Phenylalkyl $R^1$ or $R^6$ can be, for example, benzyl, 2-phenethyl, 3-phenylpropyl or 3-phenylbutyl. $C_7$–$C_{10}$-Alkylphenyl $R^6$ can be, for example, tolyl, xylyl, ethylphenyl, isopropylphenyl or tert.-butylphenyl. $C_7$–$C_{22}$-Alkylaryl $R^9$ can moreover also be, for example, methylnaphthyl, butylnaphthyl, dibutylphenyl, dioctylphenyl, nonylphenyl or dodecylphenyl.

$C_2$–$C_{12}$-Alkanoyl $R^{17}$ can be, for example, acetyl, propionyl, isobutyryl, 2-ethylbutyryl, n-octanoyl, n-decanoyl or n-dodecanoyl.

$R^4$ and $R^5$, together with the N atom to which they are bonded, can be a 5-membered or 6-membered heterocyclic ring. This can be, for example, a pyrrolidine, piperidine, morpholine or 4-methylpiperazine ring.

$C_2$–$C_{12}$-Alkylene M, $R^{10}$, $R^{12}$ or $R^{18}$ can be straight-chain alkylene, for example di-, tri-, tetra-, hexa-, octa- or dodeca-methylene, or branched alkylene, for example 1,2-propylene, 1,2-butylene, 2,2-dimethyl-1,3-propylene or 2,5,5-trimethylhexamethylene. $C_1$–$C_{12}$-Alkylene $R^{11}$ can moreover also be methylene.

$C_4$–$C_8$-Oxaalkylene $R^{10}$ can be, for example, 3-oxapent-1,5-ylene, 4-oxahept-2,6-ylene or 3,6-dioxaoct-1,8-ylene. $C_4$–$C_6$-Alkylene $R^{18}$ which is interrupted by O or NR$^{16}$ can moreover also be, for example, 3-azapent-1,5-ylene, 4-azahept-2,6-ylene or 3-(methylaza)-pent-1,5-ylene.

$C_4$–$C_8$-Alkylene M can be, for example, 2-buten-1,4-ylene, 3-hexen-1,6-ylene or 4-octen-1,8-ylene. $C_2$–$C_6$-Alkenylene $R^{11}$ can be, for example, vinylene, methylvinylene or 2-buten-1,4-ylene.

$C_6$–$C_{12}$-Cycloalkylene $R^{12}$ or $R^{18}$ can be, for example, 1,4-cyclohexylene, 1,2-cyclohexylene, 1,4-endomethylene-1,2-cyclohexylene, 1,4-dimethylenecyclohexane, 4,4'-dicyclohexylene or 1,4-decahydronaphthylene. $C_6$–$C_{12}$-Arylene $R^{11}$ or $R^{12}$ can be, for example, 1,2-phenylene, 1,3-phenylene, 1,4-phenylene, 1,4-naphthylene or 4,4'-diphenylene.

A divalent aliphatic, cycloaliphatic, aromatic or aromatic-aliphatic radical G having 6–15 C atoms can be, for example, hexa-, octa- or dodeca-methylene, 2,2,4-trimethylhexamethylene, cyclohexylene, 4,4'-dicyclohexylenemethane, 1,4-phenylene, 2,4-tolylene, 1,4-naphthylene or 4,4'-diphenylenemethane.

A trivalent aliphatic radical $R^{13}$ or $R^{19}$ having 3–10 C atoms can be, for example, propane-1,2,3-triyl, 1,1,1-trimethylene-ethane or 1,1,1-trimethylenepropane. A trivalent aromatic radical $R^{13}$ or $R^{19}$ can be, for example, benzene-1,2,4-triyl or naphthalene-1,4,5-triyl.

A quadrivalent aliphatic radical $R^{14}$ or $R^{20}$ having 4–10 C atoms can be, for example, butane-1,2,3,4-tetrayl or tetramethylenemethane. A quadrivalent aromatic radical $R^{14}$ or $R^{20}$ can be, for example, benzene-1,2,4,5-tetrayl, naphthalene-1,4,5,8-tetrayl or diphenyl-3,4,3',4'-tetrayl.

Compounds of the formula I which are preferred as stabilisers are those in which A is a sterically hindered hydroquinone monoether radical, and those compounds of the formula I in which B is a polyalkylpiperidine radical of the formula II or III, in which R is hydrogen. The latter compounds thus contain a 2,2,6,6-tetramethylpiperidine radical.

Of the hydroquinone ether derivatives, three classes are of particular importance.

(a) Compounds of the formula IV

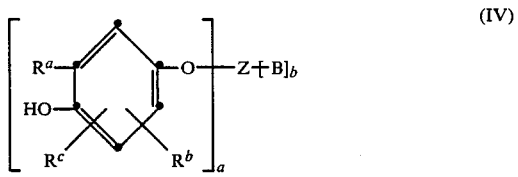

in which a and b independently of one another are numbers from 1 to 3 and (a+b) is a number from 2 to 4, $R^a$ is a monovalent hydrocarbon radical which sterically hinders the OH group, $R^b$ is hydrogen or, if a is 1, can also be a radical of the formula

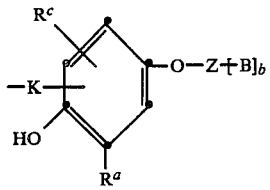

in which K is a direct bond or a divalent group of the formula —S—, —S—S—, —SO—, —SO$_2$—, —CH$_2$SCH$_2$—, —CH$_2$OCH$_2$—, —CH(R$^{21}$)— or —N(R$^{22}$)—, in which R$^{21}$ is hydrogen, C$_1$–C$_{12}$-alkyl, or C$_3$–C$_{15}$-alkyl which is interrupted by —S— or —O— and R$^{22}$ is hydrogen, C$_1$–C$_{18}$-alkyl or phenyl, R$^c$ is hydrogen or C$_1$–C$_8$-alkyl and Z and B are as defined above.

C$_1$–C$_{12}$-Alkyl R$^{21}$ can have here, for example, one of the meanings given for R$^1$. C$_1$–C$_{18}$-Alkyl R$^{22}$ can moreover also be, for example, n-tetradecyl, n-hexadecyl or n-octadecyl. C$_3$–C$_{15}$-Alkyl R$^{21}$ which is interrupted by —S— or —O— can be, for example, butylthiomethyl, 2-dodecylthioethyl, 2-methoxyethyl or 2-octyloxyethyl.

A sterically hindering hydrocarbon radical $R^a$ can be an aliphatic, cycloaliphatic, aromatic or araliphatic radical. $R^a$ is, in particular, a tertiary alkyl group having 4–12 C atoms, for example tert.-butyl, tert.-amyl (1,1-dimethylpropyl), 1,1,3,3-tetramethylbutyl or 1,1,3,3,5,5-hexamethylhexyl, or is cyclohexyl, phenyl or α,α-dimethylbenzyl.

Z in these compounds with the hydroquinone radical is bonded by an ether bond. Z is preferably an aliphatic radical with b ester or amide groups.

Preferred stabilisers of the formula IV are compounds of the formula VII

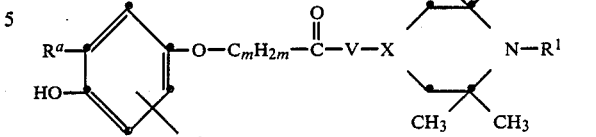

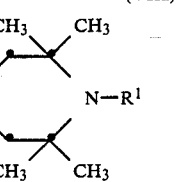

in which m is a number from 1 to 6, n, V, $R^a$ and $R^c$ are as defined for formula VII and X, Y and R$^1$ are as defined for the formulae II and III.

(b) Compounds of the formula V

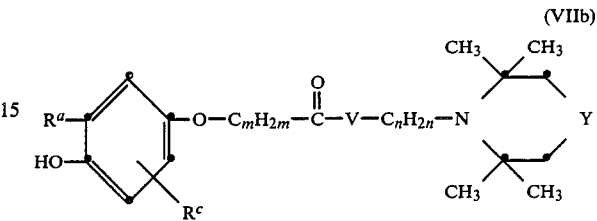

in which a, b, $R^a$, $R^b$, $R^c$, Z and B are as defined for formula IV and $R^d$ is C$_1$–C$_{20}$-alkyl, C$_3$–C$_{15}$-alkoxyalkyl, C$_5$–C$_{12}$-cycloalkyl, C$_7$–C$_{13}$-aralkyl, phenyl or a radical —C$_m$H$_{2m}$—CO—V—C$_n$H$_{2n}$—B, in which m, n and V are as defined for formula VII, or $R^d$, together with an $R^c$ in the ortho-position and the aromatic ring, is a coumaran or chroman ring, or, if a is 1, $R^d$ can also be a radical of the formula

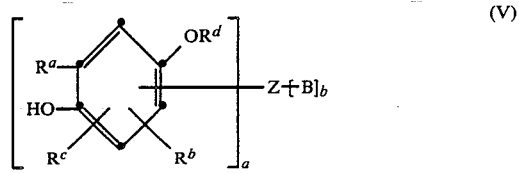

in which m is a number from 1 to 20, n is a number from 1 to 4, q is zero or 1, V is —O— or —N(R$^{22}$)—, V' is a direct bond, —O— or —N(R$^{22}$)—, a, b, $R^b$, $R^c$, R$^{22}$ and B are as defined above for formula IV and $R^a$ is a tertiary alkyl group having 4–12 C atoms, cyclohexyl, pheny or α,α-dimethylbenzyl, and, if B is a radical of the formula III, q is 1 and V' is a direct bond.

Particularly preferred compounds are those of the formula VIIa or VIIb

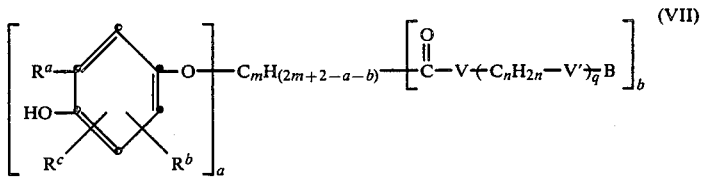

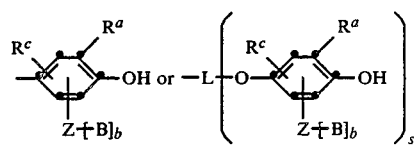

in which s is 1 or 2 and, if s is 1, L is C$_2$–C$_{12}$-alkylene, which can be interrupted by one or two O or S atoms, C$_4$–C$_{10}$-alkenylene, C$_4$–C$_6$-alkynylene, C$_5$–C$_{12}$-cycloalkylene, xylylene or a radical of the formula

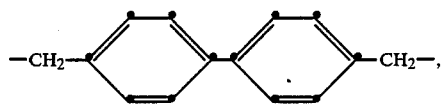

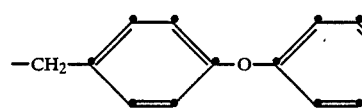

—CH$_2$—CH(OH)—CH$_2$—, —CH$_2$CH(OH)CH$_2$—O—R$^{12}$—O—CH$_2$CH(OH)CH$_2$— or —CH$_2$COO—R$^{10}$—OOC—CH$_2$, in which R$^{10}$ and R$^{12}$ are as defined above, or, if s is 2, L is a trivalent group of the formula

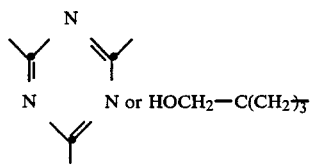

R$^d$ is a monovalent radical and can be C$_1$–C$_{20}$-alkyl, for example methyl, ethyl, isopropyl, n-butyl, isoamyl, n-hexyl, 2-ethylbutyl, n-octyl, 2-ethylhexyl, n-decyl, n-dodecyl, n-hexadecyl or n-octadecyl. R$^d$ can be C$_3$–C$_{15}$-alkoxyalkyl, for example 2-methoxyethyl, 2-butoxyethyl or 2-dodecyloxyethyl. C$_5$–C$_{12}$-Cyclohexyl R$^d$ can be, for example, cyclopentyl, cyclohexyl, methylcyclohexyl, cyclooctyl or cyclododecyl. C$_7$–C$_{13}$-Aralkyl R$^d$ can be, for example, benzyl, 2-phenethyl, 1-phenylisopropyl, 3-phenylpropyl or 2-naphthylmethyl. A coumaran or chroman ring formed by R$^d$ together with an R$^c$ in the ortho-position and the aromatic ring can be substituted by alkyl groups.

If s is 1, L is a divalent group and can be a C$_2$–C$_{12}$-alkylene group, which can be interrupted by O or S atoms. Examples are di-, tri-, tetra-, hexa-, octa- or dodecamethylene, 1,2-propylene, 1,2-butylene, 2,2-dimethyl-1,3-propylene, 2,5,5-trimethylhexamethylene, 3-oxapent-1,5-ylene, 4-thiaheptamethylene or 3,8-dioxadecamethylene. L can be C$_4$–C$_{10}$-alkenylene, for example 2-buten-1,4-ylene, 3-hexen-1,6-ylene or 4-octen-1,8-ylene, or can be C$_4$–C$_6$-alkynylene, for example 2-butyn-1,4-ylene or 3-hexyn-1,6-ylene. C$_5$–C$_{12}$-Cycloalkylene L can be, for example, 1,4-cyclohexylene, 1,5-cyclooctylene or 4,4'-dicyclohexylene.

R$^a$ is preferably a tertiary alkyl group having 4–12 C atoms, for example tert.-butyl, tert.-amyl, 1,1,3,3-tetramethylbutyl or 1,1,3,3,5,5-hexamethylhexyl, or is cyclohexyl, phenyl or α,α-dimethylbenzyl.

Z in the compounds of the formula V is bonded directly to the aromatic ring and is preferably an aliphatic radical containing b ester or amide groups.

Preferred stabilisers of the formula V are compounds of the formula VIIIa or VIIIb

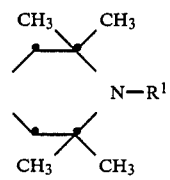

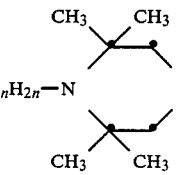

in which m is a number from 1 to 6, n is a number from 1 to 4, V is —O— or —N(R$^{22}$)—, R$^a$ is a tertiary alkyl group having 4–12 C atoms, cyclohexyl, phenyl or α,α-dimethylbenzyl, R$^d$ is as defined above, R$^{22}$ is hydrogen, C$_1$–C$_{18}$-alkyl or phenyl and X, R$^1$ and Y are as defined above for the formulae II and III.

(c) Compounds of the formula VI

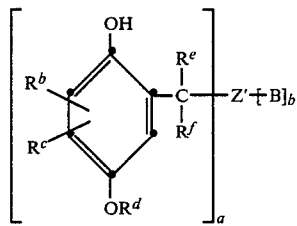

in which a, b, R$^b$ and R$^c$ are as defined for formula IV and R$^b$ can also be a radical of the formula IX

R$^d$ is as defined for formula V, R$^e$ and R$^f$ are C$_1$–C$_5$-alkyl, or the two radicals, together with the C atom to which they are bonded, are a cycloalkane or alkylcycloalkane ring or one of R$^e$ and R$^f$, together with the C atom to which it is bonded and the radical Z' or part of the radical Z', is a cycloalkane or alkylcycloalkane ring, Z' is an (a+b)-valent organic radical, Z" is a 2-valent organic radical and B is as defined in formula I.

C$_1$–C$_5$-Alkyl R$^e$ or R$^f$ can be, for example, methyl, ethyl, n-propyl, n-butyl or isobutyl. R$^e$ and R$^f$ are preferably methyl. A cycloalkane or alkylcycloalkane ring formed by R$^e$ and R$^f$ together with the C atom to which they are bonded can be, for example, a cyclopentane, cyclohexane, methylcyclohexane, dimethylcyclohexane or cyclooctane ring, preferably a cyclohexane ring.

It is also possible for only one of the radicals R$^e$ and R$^f$ to be part of a ring system, in this case together with the radical Z' or a part of the radical Z'. The ring system is cycloaliphatic and is, in particular, a cyclohexane or alkylcyclohexane ring.

In all cases, the C atom in the compounds of the formula VI to which $R^e$ and $R^f$ are bonded is a tertiary C atom, and the tertiary group thereby formed causes steric hindrance of the phenolic OH group.

Preferred stabilisers of the formula VI are those in which a is 1 and $Z'$ is an aliphatic radical containing b ester or amide groups, in particular compounds of the formula X

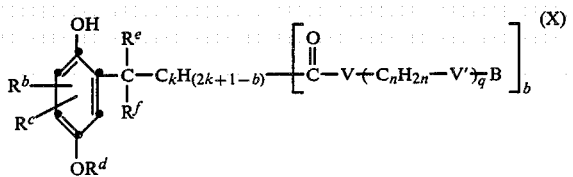

in which k is zero or a number from 1 to 20, n is a number from 1 to 4, q is zero or 1, V is —O— or —N($R^{2-2}$)—, V' is a direct bond, —O— or —N($R^{22}$)— and b, B, $R^b$, $R^c$, $R^d$, $R^e$ and $R^f$ are as defined above for formula VI, and, if B is a radical of the formula III, q is 1 and V' is a direct bond.

Particularly preferred stabilisers of the formula VI are compounds of the formula IXa or XIb

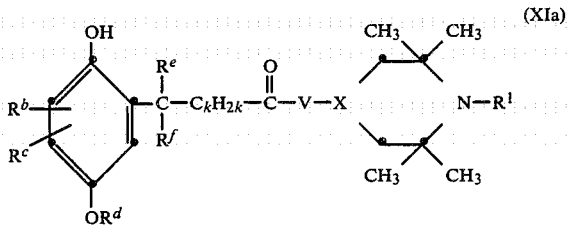

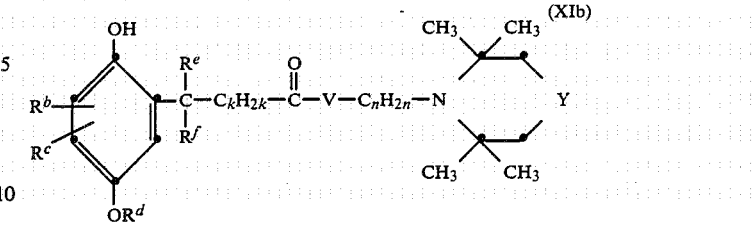

in which k is zero or a number from 1 to 6, $R^b$ is hydrogen or a group of the formula Ixa or Ixb

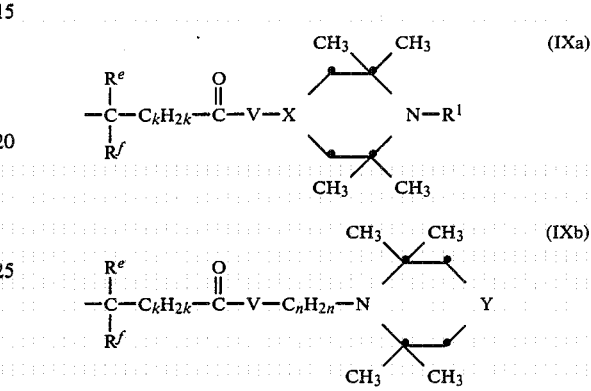

$R^e$ and $R^f$ are alkyl, n, $R^c$, $R^d$ and V are as defined above and X, $R^1$ and Y are as defined for the formulae II and III.

Examples of compounds of the formula IV are the compounds of the following formulae

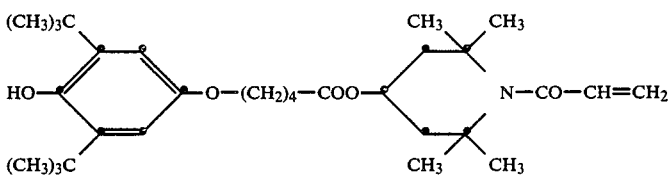

1.

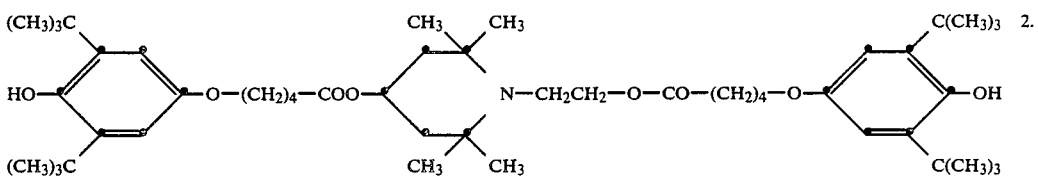

2.

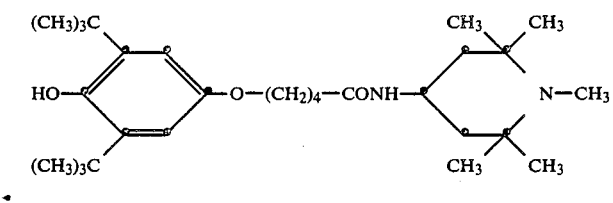

3.

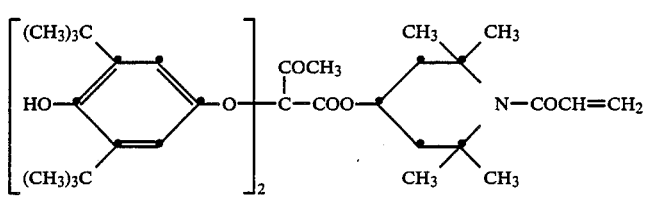
4.
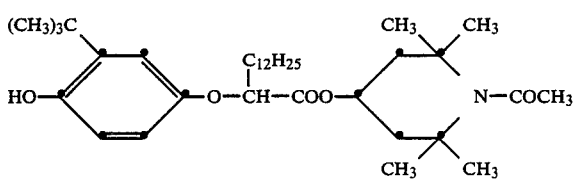
5.
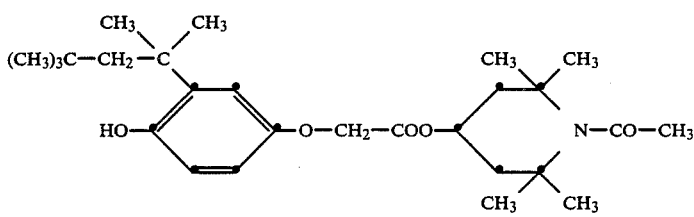
6.
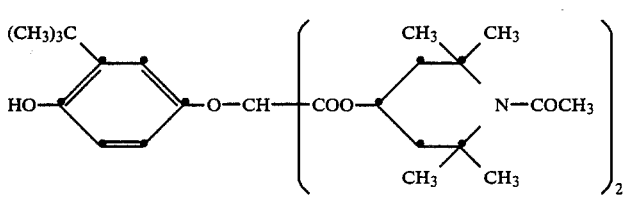
7.
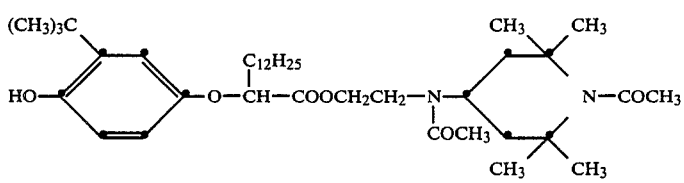
8.
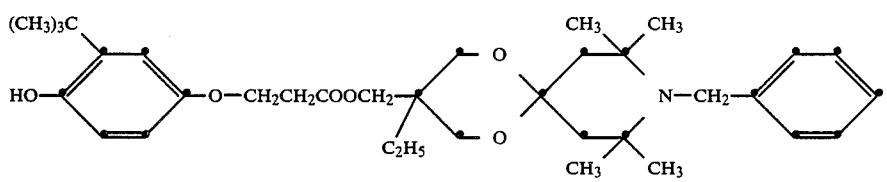
9.
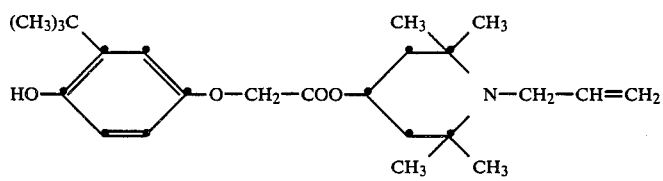
10.
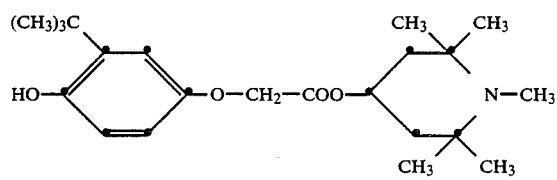
11.

-continued
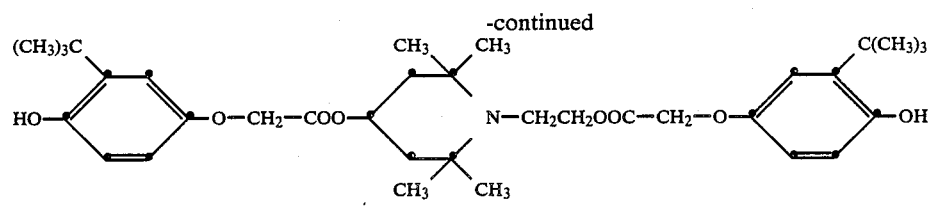 12.
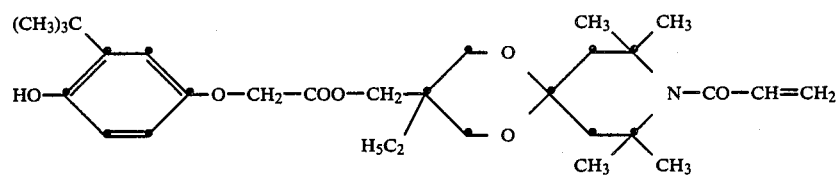 13.
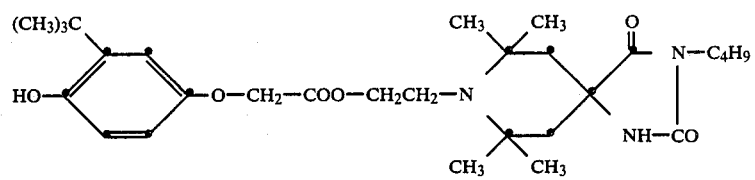 14.
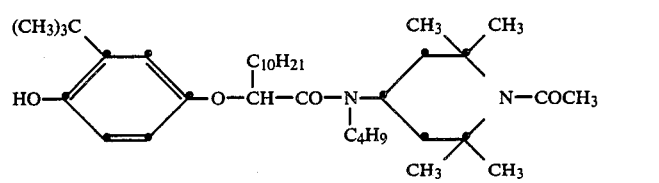 15.
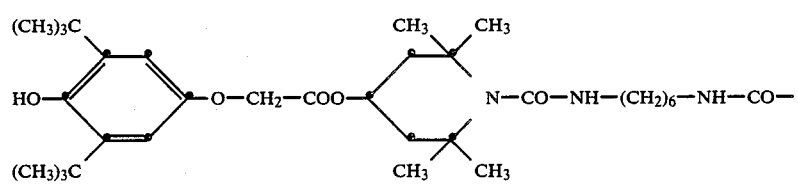 16.
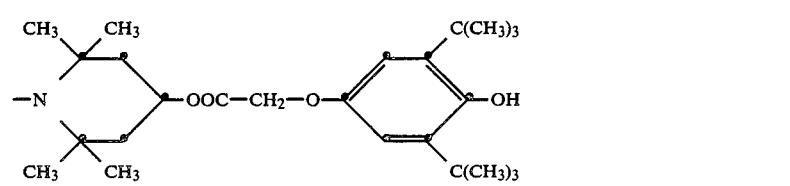
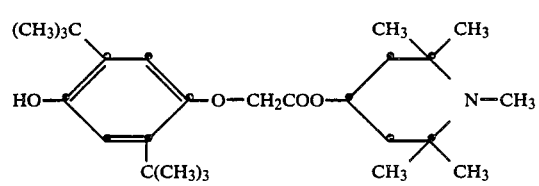 17.
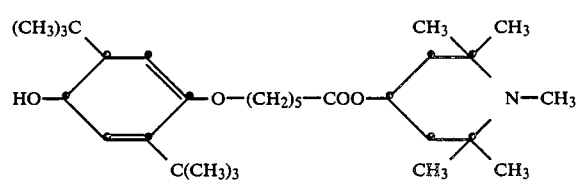 18.
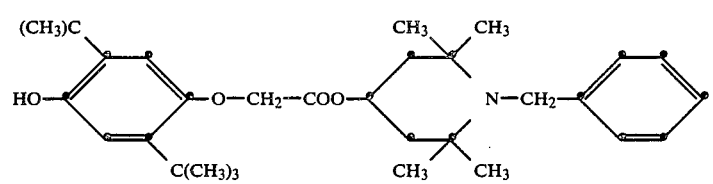 19.

Examples of compounds of the formula V are the compounds of the following formulae:
Examples of compounds of the formula VI are the compounds of the following formulae:
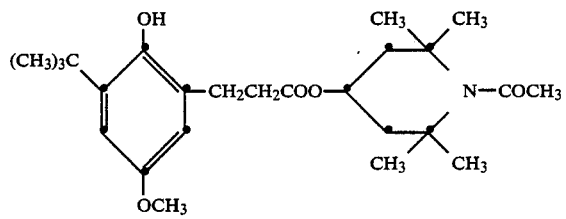
20.
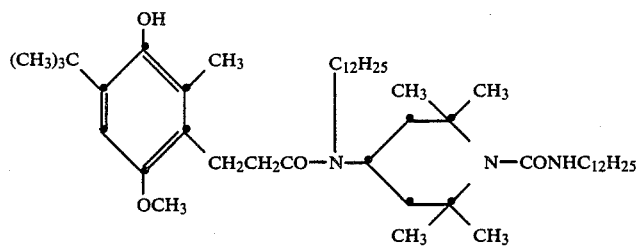
21.
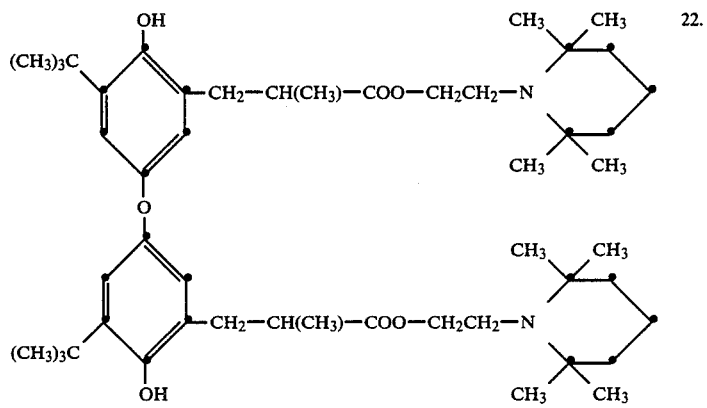
22.
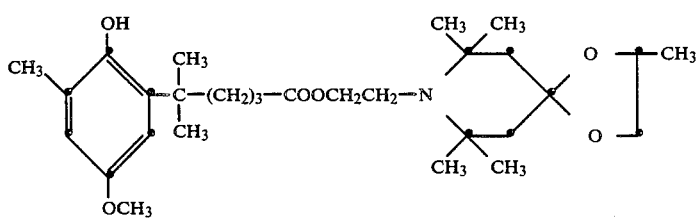
23.
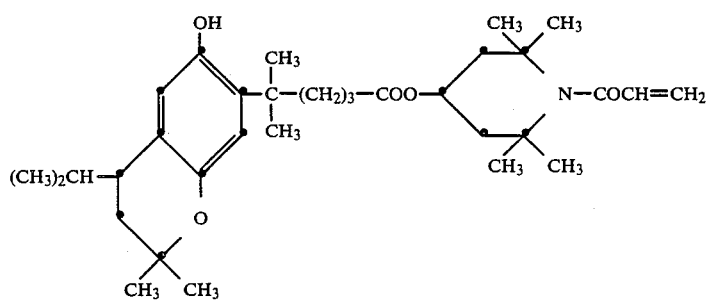
24.

-continued
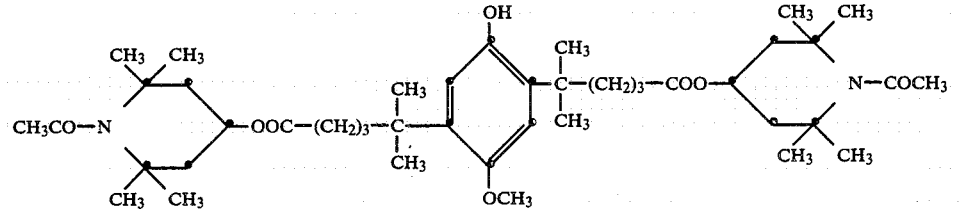
25.
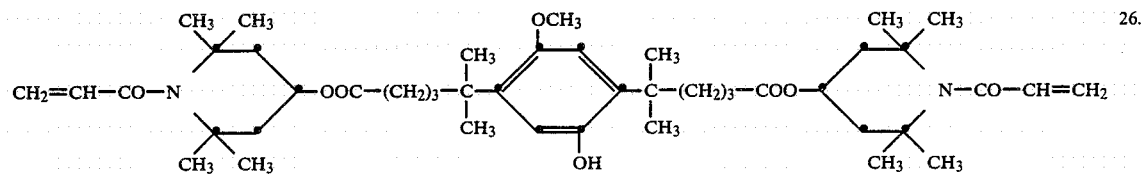
26.
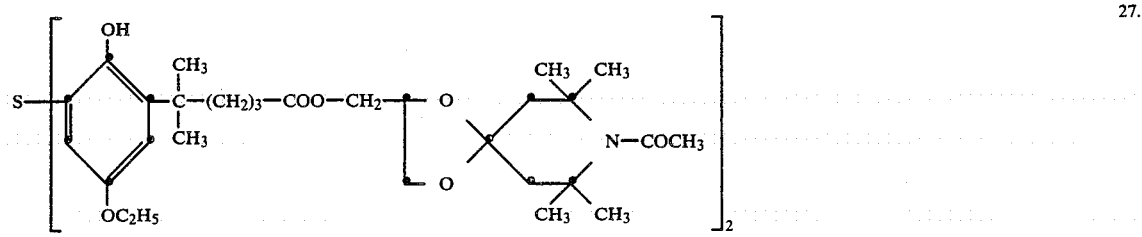
27.
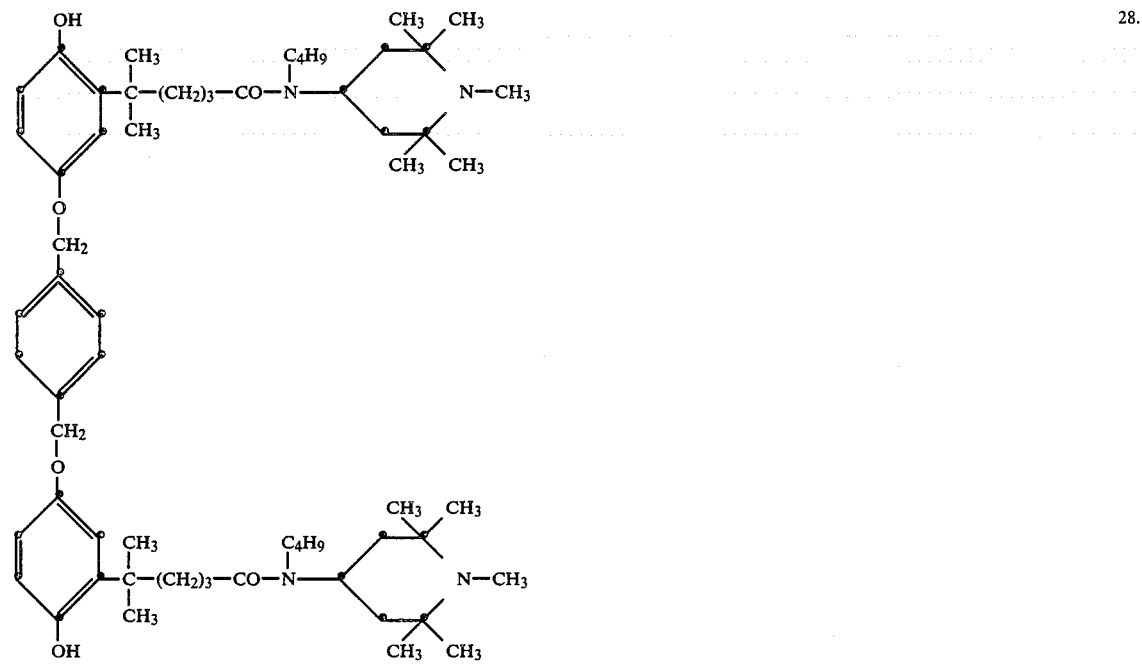
28.
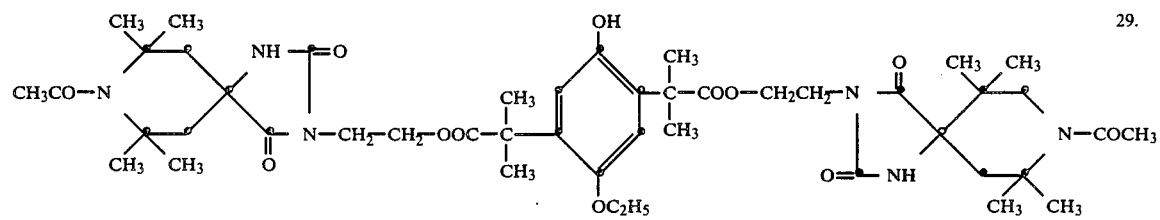
29.

-continued
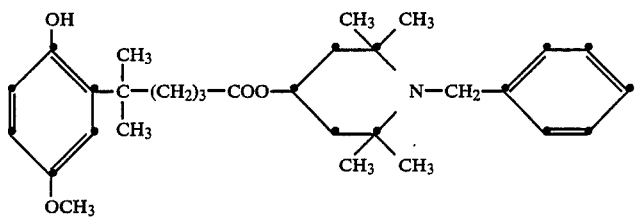
30.
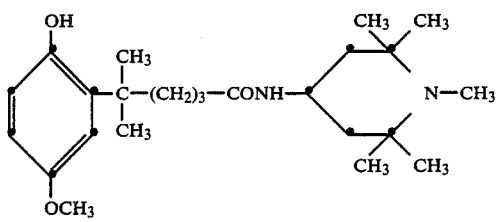
31.
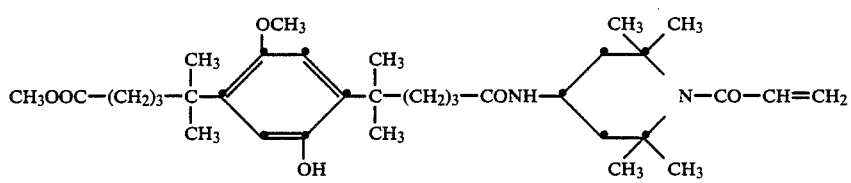
32.
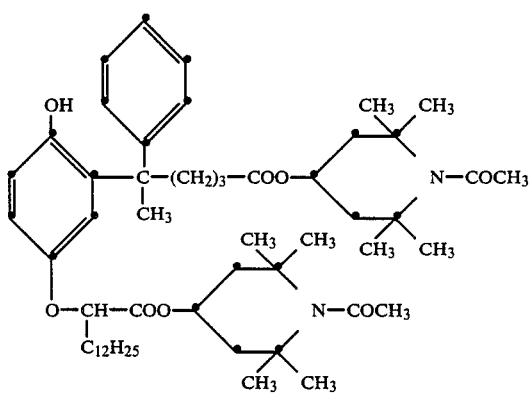
33.
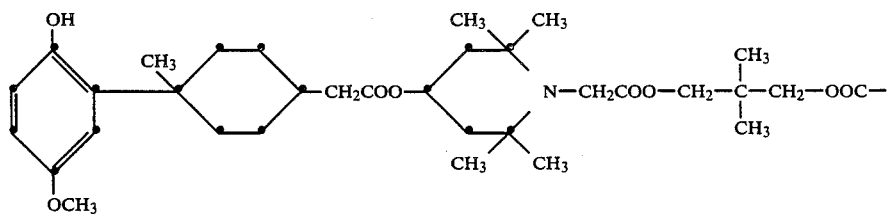
34.
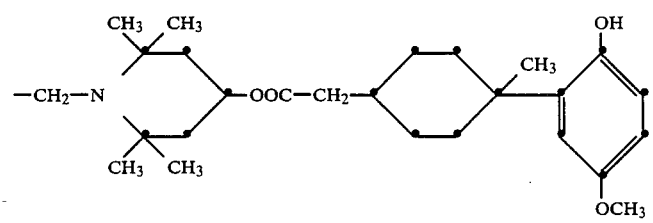

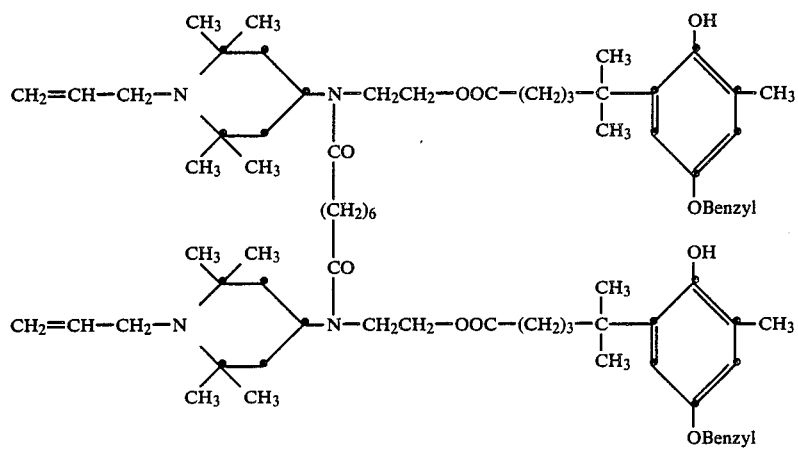
35.
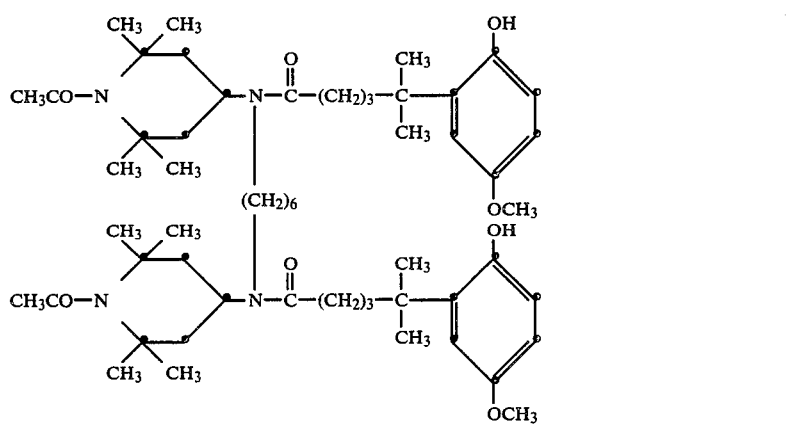
36.
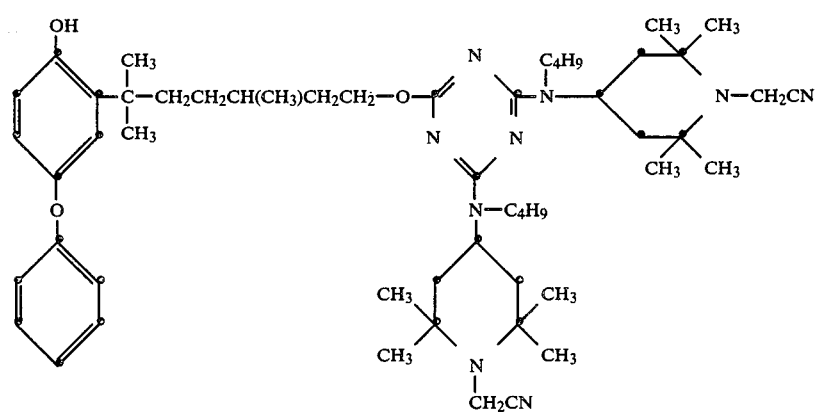
37.
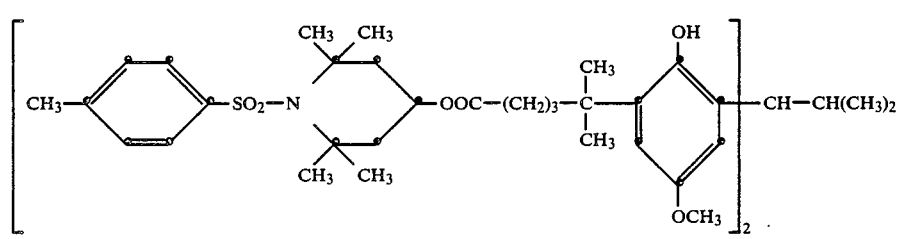
38.

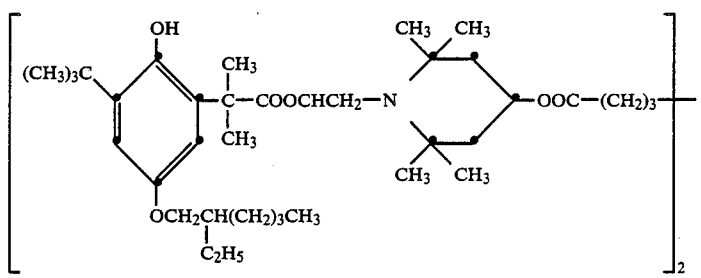

39.

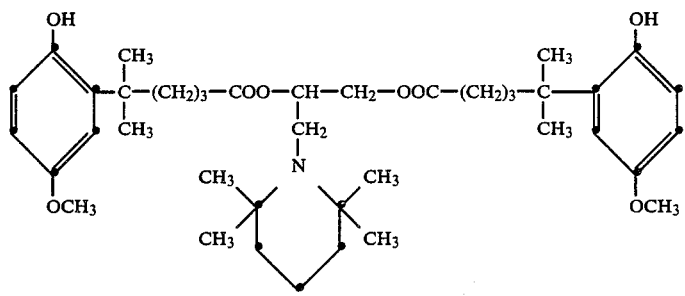

40.

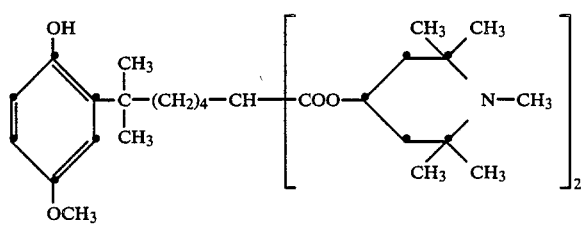

41.

The compounds of the formula I are novel compounds and as such are likewise the subject of the invention. They can be prepared by various methods, the principle of which is usually linkage of the radicals A to the radicals B via the bonding member Z.

Thus, for example, compounds of the formula IV can be prepared by etherification of a moles of a hydroquinone of the formula XII with a halogen compound XIII (Hal=halogen)

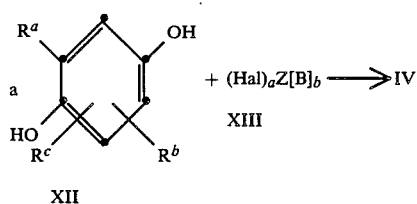

in the presence of a moles of a base by the conventional methods of etherification of phenols.

Alternatively, however, it is also possible first to etherify the hydroquinone with a halogen compound which has an additional reactive group, and to bond the radical B to Z via this group in a second reaction step. This group can be, in particular, an ester or amide group. This two-stage process can be described by formulae as follows for the preparation of compounds of the formula VII:

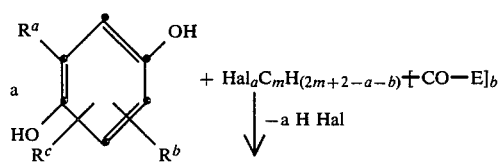

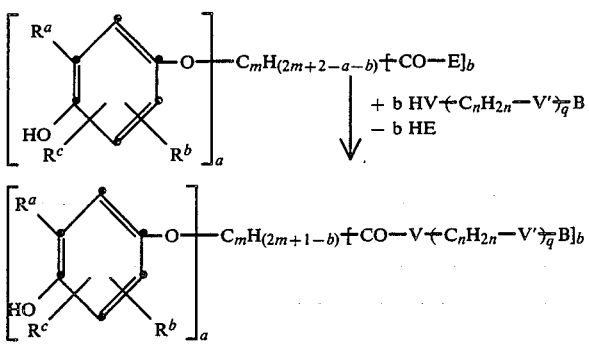

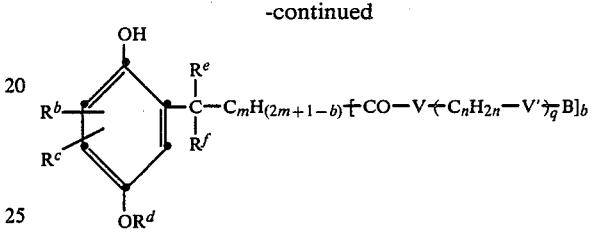

In these formulae, E is hydroxyl or halogen, but is preferably alkoxy having 1–4 C atoms.

Compounds of the formula V in which Z contains an ester or amide group can be prepared in a similar manner by esterification or amidation of a hydroquinone monoethercarboxylic acid with an HO or $R^{22}$ NH derivative of a polyalkylpiperidine.

For example, the preparation of compounds of the formula VIIIa proceeds according to the following equation:

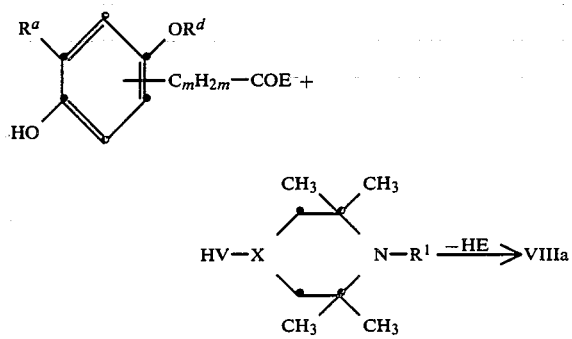

One variant is to carry out this reaction with a nonetherified hydroquinone compound ($R^d$=H) and then to introduce the radical $R^d$ by partial etherification. This variant is particularly recommended if $R^d$ is a divalent or trivalent radical.

Compounds of the formula VI in which Z' contains ester or amide groups can be prepared in an analogous manner. In the case of preparation of compounds of the formula X, the reaction proceeds according to the following equation:

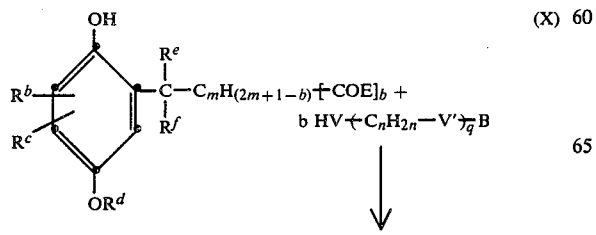

(X)

In this case also, $R^d$ can be introduced either before or after introduction of B.

Alternatively, introduction of the radical $R^1$ can also be carried out as the last step of the synthesis of all the compounds of the formula I. This introduction is effected by the conventional methods for N-substitution of sterically hindered piperidines, which are described in detail in many patent specifications.

Overall, the synthesis of compounds of the formula I is always a multi-stage operation and the sequence of the individual steps can be appropriately varied in each individual case.

The stabilisers according to the invention can be incorporated into a photographic material in a known manner by themselves or together with other compounds.

As a rule, the stabilisers are incorporated into the photographic material, by themselves or together with other compounds, in particular with colour couplers, in the form of a dispersion, this dispersion containing either no solvent or high-boiling or low-boiling solvents or a mixture of such solvents. Another suitable incorporation variant comprises incorporating the stabilisers into the photographic material, by themselves or together with other compounds, together with a polymer in the form of a latex.

The dispersions are then used for the preparation of the layers of colour-photographic recording materials. These layers can be, for example, interlayers or protective layers, but in particular are photosensitive (blue-, green- and red-sensitive) silver halide emulsion layers in which the blue-green (cyan), purple (magenta) and yellow dyes are formed from the corresponding colour couplers on development of the exposed recording material. The silver halide layers can contain any colour couplers, in particular blue- green, purple and yellow couplers, which are used for formation of the dyes mentioned and hence the colour images.

Since the substrate influences the action and stability of the stabilisers, substrates (solvents, polymers) which, together with the stabilisers, give as high a stability as possible of the materials to be stabilised are preferred.

As a rule, the stabilisers are incorporated into layers which additionally contain a silver halide dispersion prepared and sensitised by conventional methods. However, they can also be contained in layers adjacent to layers containing silver halide.

The photographic materials according to the invention have a conventional build-up and contain components which intensify the activity of the stabilisers or at least do not adversely affect it.

In the photographic recording material according to the present invention, the stabilisers can additionally also be combined with ultraviolet absorbers or other light stabilisers in the same layer, as well as with the colour couplers. If the diffusion transfer method is used, the stabiliser can also be incorporated into a receiving layer.

The colour-photographic materials according to the invention can be processed in a known manner. During or after processing, they can also be treated in a manner such that their stability is increased further, for example by treatment in a stabiliser bath or application of a protective coating.

In certain cases, the stabilisers to be used according to the invention are also suitable for protecting colour-photographic layers, in which the dyes are incorporated directly into the emulsion and the image is produced by selective bleaching.

The amount of stabiliser or stabilisers can vary within wide limits, and is, for example, in the range from 1 to 2,000 mg, preferably 100 to 800 and in particular 200–500 mg, per m² of the layer into which it (they) is (are) incorporated.

If the photographic material contains one or more UV absorbers, this can be present with the stabiliser together in one layer or in an adjacent layer. The amount of UV absorber can vary within wide limits and is, for example, in the range from 200–2,000 mg, preferably 400–1,000 mg, per m² of the layer. Examples of suitable UV absorbers are those of the benzophenone, acrylonitrile, thiazolidone, benzotriazole, oxazole, thiazole and imidazole types.

The colour images obtained with the recording material according to the invention by exposure and development have a very good light-fastness towards visible and ultraviolet light. The stabiliser according to the invention are virtually colourless, so that no discoloration of the images occurs; in addition, they are particularly compatible with the conventional photographic additives present in the individual layers. Because of their good activity, the amount used thereof can be reduced, and precipitation or crystallisation thereof when they are incorporated as an organic solution into the aqueous binder emulsions used for the preparation of photographic layers is thus avoided. The individual process steps which are required for the preparation of the coloured images after exposure of the photographic recording material are not adversely influenced by the stabilisers. Furthermore, the so-called abrasion fog formation which frequently occurs with blue-sensitive emulsions can be substantially suppressed. This abrasion fog may form, for example, if photographic materials (silver halide emulsion layers on a carrier of natural or synthetic materials) are subjected to mechanical stress, for example twisting, bending or rubbing, during preparation or during treatment before development. (T. H. James, The Theory of Photographic Process 4th edition, Macmillan, New York, N.Y. 1977, page 23 et seq., page 166 et seq.).

The examples which follow illustrate the preparation of the compounds according to the invention and their use in a colour-photographic recording material. The temperatures in these examples are given in °C.

EXAMPLE 1

33.2 g of tert.-butyl hydroquinone, 41.35 g of methyl bromoacetate and 37.3 g of potassium carbonate (anhydrous) are refluxed in 300 ml of acetone under nitrogen for 3 days. The solvent is removed under reduced pressure and 500 ml of ether are added. This ether solution is washed with water, dried with magnesium sulfate and evaporated. The residue is distilled in vacuo. The brown distillate obtained at 138°–140° under $10^{-3}$ mm Hg is purified by means of column chromatography. The methyl 2-(3-tert.-butyl-4-hydroxyphenoxy)-acetate thus obtained can be crystallised from hexane. Melting point: 87°–89°.

2.38 g of this compound, 2.0 g of 1-allyl-4-hydroxy-2,2,6,6-tetramethylpiperidine and 0.1 g of dibutyl-tin oxide are refluxed in 80 ml of xylene. An azeotropic methanol xylene mixture is slowly distilled off over a period of three hours. The residual solvent is evaporated off under reduced pressure and the residue is purified by column chromatography. 1-Allyl-2,2,6,6-tetramethylpiperidin-4-yl 2-(3-tert.-butyl-4-hydroxyphenoxy)-acetate is thus obtained as a slightly brown oil (Compound No. 10).

The procedure described above is repeated using a corresponding amount of 1-methyl-4-hydroxy-2,2,6,6-tetramethylpiperidine instead of 1-allyl-4-hydroxy-2,2,6,6-tetramethylpiperidine. 1-Methyl-2,2,6,6-tetramethylpiperidin-4-yl 2-(3-tert.-butyl-4-hydroxy-phenoxy)-acetate is obtained as a slightly brown oil (Compound No. 11).

1-[2-(3-tert.-Butyl-4-hydroxyphenoxyacetoxy)-ethyl]-4-(3-tert.-butyl-4-hydroxyphenoxyacetoxy)-2,2,6,6-tetramethylpiperidine is obtained as white crystals of melting point 74°–77° (Compound No. 12) in a similar manner by reacting methyl 3-tert.-butyl-4-hydroxy-phenoxy-acetate with 1-(2-hydroxyethyl)-4-hydroxy-2,2,6,6-tetramethylpiperidine in a molar ratio of 2:1.

8-[2-(3-tert.-Butyl-4-hydroxyphenoxyacetoxy)-ethyl]-3-butyl-7,7,9,9-tetramethyl-2,4-dioxo-1,3,8-triaza-spiro[4.5]decane of melting point 177°–179° (Compound No. 14) is obtained similarly from the above methyl ester and 3-butyl-7,7,9,9-tetramethyl-8-(2-hydroxyethyl)-2,4-dioxo-1,3,8-triaza-spiro[4.5]decane in a molar ratio of 1:1.

3-(3-tert.-Butyl-4-hydroxyphenoxyacetoxymethyl)-3-ethyl-8,8,10,10-tetramethyl-1,5-dioxa-9-aza-spiro[5.5]undecane is obtained as a light brown oil similarly from the above methyl ester and 3-ethyl-3-hydroxymethyl-8,8,10,10-tetramethyl-1,5-dioxa-9-aza-spiro[5.5]undecane in a molar ratio of 1:1. 3.75 g of this compound are dissolved in 60 ml of ethyl acetate. After addition of 0.9 g of trimethylamine, the solution is cooled to −5° and a solution of 0.75 g of acrylyl chloride in 10 ml of ethyl acetate is added dropwise. The mixture is stirred at −5° for 3 hours and then warmed to room temperature. The solution is washed with water, dried and evaporated. The residue is purified by column chromatography. The N-acryloyl compound (Compound No. 13) is thus obtained as white crystals of melting point 163°-165°.

EXAMPLE 2

Ethyl 2-(3-tert.-butyl-4-hydroxyphenoxy)-tetradecanoate is obtained as white crystals of melting point 51°-53° from ethyl 2-bromotetradecanoate and tert.-butyl hydroquinone in a procedure similar to that described in Example 1.

21 g of this compound, 10 g of 1-acetyl-4-hydroxy-2,2,6,6-tetramethylpiperidine and 0.5 g of dibutyl-tin oxide are refluxed in 250 ml of xylene. The ethanol formed is distilled off in an azeotrope with xylene over a period of 24 hours. The resulting solution is evaporated in vacuo and the residue is purified by column chromatography. 1-acetyl-2,2,6,6-tetramethyl-4-piperidinyl 2-(3-tert.-butyl-4-hydroxyphenoxy)-tetradecanoate (Compound No. 5) is thus obtained as white crystals of melting point 106°-108°.

EXAMPLE 3

8 g of 2,5-bis-(5-methoxycarbonyl-2-methylpent-2-yl)-4-methoxyphenol, 6.3 g of 4-hydroxy-2,2,6,6-tetramethylpiperidine and 0.2 g of dibutyl-tin oxide are refluxed in 150 ml of xylene. The methanol formed is distilled off in an azeotrope with xylene over a period of 6 hours. The residual xylene is distilled off in vacuo and the residue is recrystallised from acetonitrile to give 2,5-bis[5-(2,2,6,6-tetramethylpiperidin-4-yloxycarbonyl)-2-methyl-pent-2-yl]-4-methoxyphenol as white crystals of melting point 165°-168°.

5.3 g of this compound are dissolved in 50 ml of ethyl acetate. After addition of 2 g of triethylamine, the solution is cooled to −5° and a solution of 1.5 g of acrylyl chloride in 10 ml of ethyl acetate is added dropwise. The mixture is stirred at −5° for one hour and at 0° for a further hour. The resulting solution is washed with 1N hydrochloric acid and with water, dried and evaporated. The residue is purified by column chromatography. 2,5-Bis[5-(1-acryloyl-2,2,6,6-tetramethylpiperidin-4-yloxycarbonyl)-2-methylpent-2-yl]-4-methoxyphenol are obtained as white crystals of melting point 50°-52° (Compound No. 26).

EXAMPLE 4

0.087 g of the yellow coupler of the formula

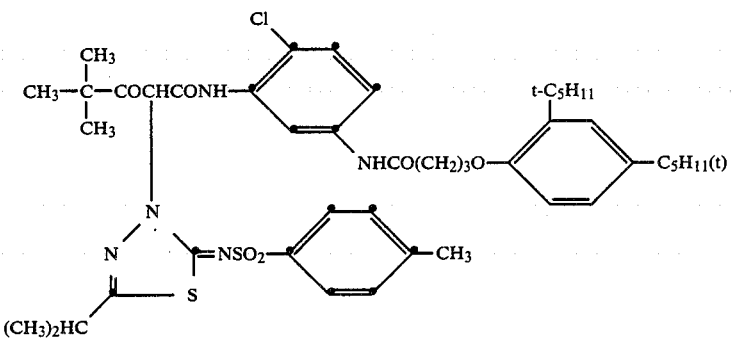

and 0.026 g of one of the stabilisers shown in the table which follows are dissolved in 2.0 ml of a mixture of tricresyl phosphate/ethyl acetate (1.5 g in 10 ml). 7.0 ml of a 6% gelatin solution, 0.5 ml of an 8% solution of the wetting agent of the formula

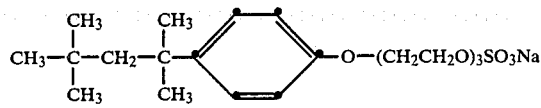

in isopropanol/water (3:4) and 0.5 ml of water are added to this solution and the components are emulsified with ultrasound at an output of 100 watt for 5 minutes.

2.0 ml of a silver bromide emulsion with a silver content of 6.0 g per liter, 0.7 ml of a 1% aqueous solution of the hardener of the formula

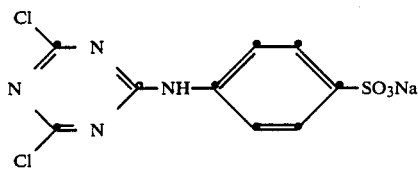

and 3.8 ml of water are added to 2.5 ml of the emulsion thus obtained and the mixture is brought to a pH value of 6.5 and coated onto subbed plastic-coated white paper mounted on a glass plate.

After solidification, the paper is dried in a drying cabinet with circulating air at room temperature.

After 7 days, samples cut to 35 × 180 mm are exposed behind a step wedge with 3,000 lux.s and are then processed in the Kodak Ektaprint ®2 process.

The yellow wedges thus obtained are irradiated in an Atlas Weather-Ometer with a 2,500 W xenon lamp with a total of 42 kJoules/cm² (a comparison sample contains no light stabiliser). The loss in colour density which thereby occurs is determined by measuring the colour density at $\lambda_{max}$ with a densitometer (TR 924 A from Macbeth).

The results are shown in the following table.

| Stabiliser Compound No. | Percentage loss in colour density |
| --- | --- |
| 5 | 24 |
| 13 | 19 |
| 14 | 20 |
| 26 | 23 |
| without a stabiliser | 36 |

What is claimed is:

1. A compound of the formula $$[A]_aZ\text{—}B]_b \quad (I)$$

in which a and b independently of one another are integers from 1 to 5 and (a+b) is a number from 2 to 6, A is a monovalent hydroquinone monoether or resorcinol monoether radical, the free OH group of which is sterically hindered, Z is an (a+b)-valent organic radical linking groups A and B and B is a monovalent polyalkylpiperidine radical of the formula II or III

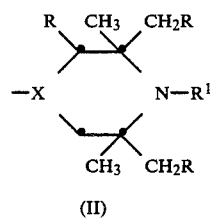 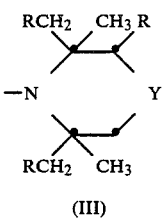

(II)                                      (III)

in which R is hydrogen or methyl, X is a group

or a 5-membered or 6-membered heterocyclic spiro ring with two O or N atoms, Y is a group —CH₂— or —CH(R²)— or a 5-membered or 6-membered heterocyclic spiro ring with two O or N atoms, R¹ is hydroxyl, $C_1$–$C_{12}$-alkyl, $C_3$–$C_6$-alkenyl, $C_3$–$C_4$-alkynyl, $C_7$–$C_{12}$-phenylalkyl, glycidyl, $C_1$–$C_4$-alkyl which is substituted by halogen, —CN, —COOR³ or —CON(R⁴)(R⁵), a group —CO—R⁶, —CO—OR³, —CO—N(R⁴)(R⁵), —CH₂—CH(R⁷)—OR⁸, —SO—R⁹, —SO₂—R⁹, —OR³ or —OOC—R⁶, or a group —Zº—A, in which Zº is a divalent organic radical, and, if b is 1, R¹ can also be a group of the formula

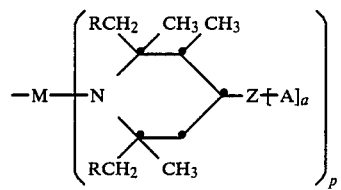

in which p is 1, 2 or 3 and, if p is 1, M is a divalent group and is $C_2$–$C_{12}$-alkylene, $C_4$–$C_8$-alkenylene, xylylene or a radical of the formula —CH₂C≡C—CH₂—)

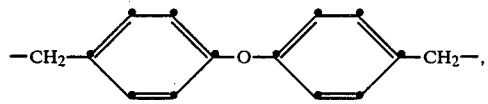

—CH₂—COO—R¹⁰—OOC—CH₂—, —CH₂—CH(OH)—CH₂—, —CH₂CH(OH)CH₂—D—CH₂CH(OH)CH₂—, —CH₂—CH(R⁷)—OOC—R¹¹—COO—CH(R⁷)—CH₂— or —CO—NH—G—NH—CO—, in which D is a divalent radical of the formula —O—R¹²—O— or —OOC—R¹¹—COO— and G is a divalent aliphatic, cycloaliphatic, aromatic or aromatic-aliphatic radical having 6–15 C atoms, or, if p is 2, M is a trivalent radical of the formula

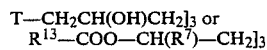

in which T is a trivalent radical of the formula

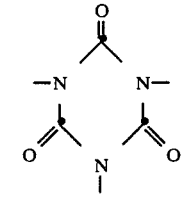

or, if p is 3, M is a quadrivalent radical of the formula

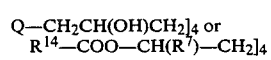

in which Q is a group of the formula

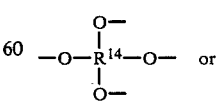

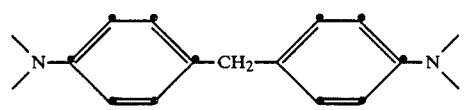

$R^2$ is hydroxyl, —$OR^{15}$, —OOC—$R^6$, —OOC—N($R^4$)($R^5$), —N($R^{16}$)—CO—$R^6$ or —N($R^{16}$)—CO—N($R^4$)($R^5$), or is a group —$Z^o$—A, and, if b is 1, $R^2$ can also be a group of the formula

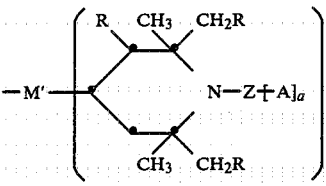

in which r is 1, 2 or 3 and, if r is 1, M' is a divalent group of the formula —OOC—$R^{11}$—COO—, —OOC—NH—G—NH—COO—, —N($R^{16}$)—CO—$R^{11}$—CO—N—($R^{16}$)— or —N($R^{17}$)—$R^{18}$—N($R^{17}$)—, or, if r is 2, M' is a trivalent group of the formula $R^{19}$[COO]$_3$ or $R^{19}$[CON($R^{16}$)]$_3$ or, if r is 3, M' is a quadrivalent group of the formula $R^{20}$[COO]$_4$ or $R^{20}$[CON($R^{16}$)]$_3$ $R^3$ is $C_1$–$C_{12}$-alkyl, benzyl or cyclohexyl, $R^4$ is $C_1$–$C_{12}$-alkyl, allyl, cyclohexyl, benzyl or phenyl and $R^5$ is hydrogen, $C_1$–$C_8$-alkyl or allyl, or $R^4$ and $R^5$, together with the N atom, are a 5-membered or 6-membered heterocyclic ring, $R^6$ is hydrogen, $C_1$–$C_{12}$-alkyl, $C_2$–$C_6$-alkenyl, chloromethyl, $C_5$–$C_{12}$-cycloalkyl, $C_7$–$C_{12}$-phenylalkyl, phenyl, $C_7$–$C_{10}$-alkylphenyl, or phenyl, phenylmethyl or phenethyl which is substituted by 1 or 2 $C_1$–$C_4$-alkyl groups and a hydroxyl group, $R^7$ is hydrogen, $C_1$–$C_4$-alkyl, $C_2$–$C_{13}$-alkoxymethyl, phenyl or phenoxymethyl, $R^8$ is hydrogen, $C_1$–$C_{12}$-alkyl, —CO—$R^6$ or —CO—N($R^4$)($R^5$), $R^9$ is $C_1$–$C_{12}$-alkyl, phenyl or $C_7$–$C_{22}$-alkylaryl, $R^{10}$ is $C_2$–$C_{12}$-alkylene, $C_4$–$C_8$-oxaalkylene or cyclohexylene, $R^{11}$ is a direct bond, $C_1$–$C_{12}$-alkylene, $C_2$–$C_6$-alkenylene, $C_6$–$C_{12}$-cycloalkylene or -cycloalkenylene or $C_6$–$C_{12}$-arylene, $R^{12}$ is $C_2$–$C_{12}$-alkylene, $C_6$–$C_{12}$-cycloalkylene, $C_6$–$C_{12}$-arylene or -phenylene-W-phenylene- and W is —O—, —CH$_2$—, >C(CH$_3$)$_2$ or —SO$_2$—, $R^{13}$ is a trivalent aliphatic hydrocarbon radical having 3–10 carbon atoms or a trivalent aromatic hydrocarbon radical having 6–10 C atoms, $R^{14}$ is a quadrivalent aliphatic hydrocarbon radical having 4–10 C atoms or a quadrivalent aromatic hydrocarbon radical having 6–12 C atoms, $R^{15}$ is hydrogen, $C_1$–$C_{12}$-alkyl, allyl or benzyl, $R^{16}$ is hydrogen, $C_1$–$C_{12}$-alkyl, $C_5$–$C_{12}$-cycloalkyl or benzyl, $R^{17}$ is hydrogen, $C_1$–$C_{12}$-alkyl, allyl, benzyl, $C_2$–$C_{12}$-alkanoyl or benzoyl, $R^{18}$ is $C_2$–$C_{12}$-alkylene, $C_4$–$C_{16}$-alkylene which is interrupted by one or more —O— or —N($R^{16}$)—, or $C_6$–$C_{12}$-cycloalkylene, $R^{19}$ is a trivalent aliphatic radical having 3–10 C atoms, a trivalent aromatic radical having 6–10 C atoms or the group N(CH$_2$)$_3$ and $R^{20}$ is a quadrivalent aliphatic radical having 4–10 C atoms or a quadrivalent aromatic radical having 6–12 C atoms.

2. A compound according to claim 1 of the formula

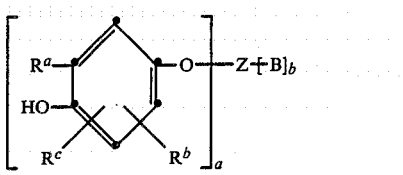

in which a and b independently of one another are numbers from 1 to 3 and (a+b) is a number from 2 to 4, $R^a$ is a monovalent hydrocarbon radical which sterically hinders the OH group, $R^b$ is hydrogen or, if a is 1, can also be a radical of the formula

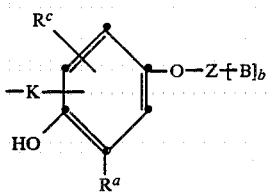

in which K is a direct bond or a divalent group of the formula —S—, —S—S—, —SO—, —SO$_2$—, —CH$_2$SCH$_2$—, —CH$_2$OCH$_2$—, —CH($R^{21}$)— or —N($R^{22}$)—, in which $R^{21}$ is hydrogen, $C_1$–$C_{12}$-alkyl, or $C_3$–$C_{15}$-alkyl which is interrupted by —S— or —O— and $R^{22}$ is hydrogen, $C_1$–$C_{18}$-alkyl or phenyl, $R^c$ is hydrogen or $C_1$–$C_8$-alkyl and Z and B are as defined in claim 1.

3. A compound according to claim 1 of the formula

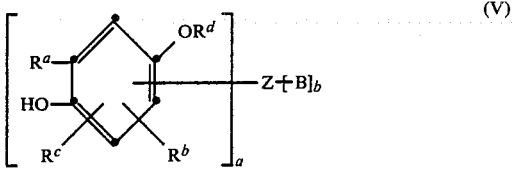

in which Z and B are as defined in claim 1, a, b, $R^a$, $R^b$ and $R^c$ are as defined in claim 2 and $R^d$ is $C_1$–$C_{21}$-alkyl, $C_3$–$C_{15}$-alkoxyalkyl, $C_5$–$C_{12}$-cycloalkyl, $C_7$–$C_{13}$-aralkyl, phenyl or a radical —$C_mH_{2m}$—CO—V—$C_nH_{2n}$—B, in which m is a number from 1 to 20, n is a number from 1 to 4 and V is —O— or —N($R^{22}$)— wherein $R^{22}$ is hydrogen, $C_1$–$C_{18}$-alkyl or phenyl, or $R^d$ together with an $R^c$ in the ortho-position and the aromatic ring, is a coumaran or chroman ring, or, if a is 1, $R^d$ can also be a radical of the formula

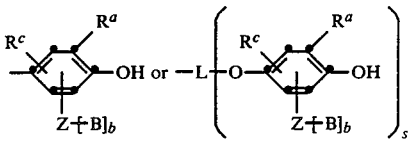

in which s is 1 or 2 and, if s is 1, L is $C_2$–$C_{12}$-alkylene, which can be interrupted by one or two O or S atoms, $C_4$–$C_{10}$-alkenylene, $C_4$–$C_6$-alkynylene, $C_5$–$C_{12}$-cycloalkylene, xylylene or a radical of the formula

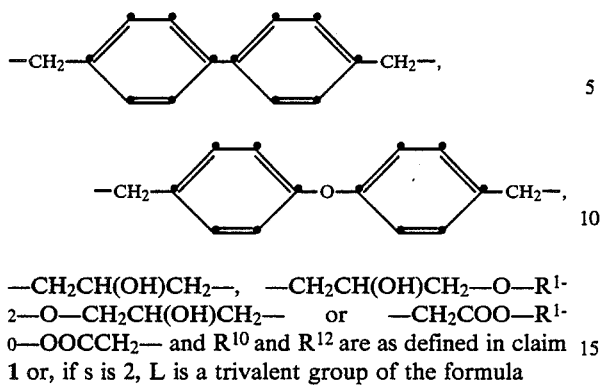

—CH$_2$CH(OH)CH$_2$—, —CH$_2$CH(OH)CH$_2$—O—R$^{12}$—O—CH$_2$CH(OH)CH$_2$— or —CH$_2$COO—R$^{10}$—OOCCH$_2$— and R$^{10}$ and R$^{12}$ are as defined in claim 1 or, if s is 2, L is a trivalent group of the formula

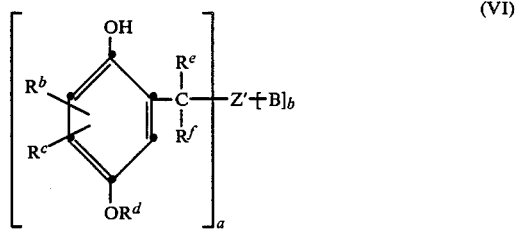

4. A compound according to claim 1 of the formula

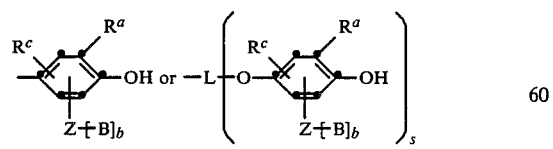

(VI)

wherein

Z' is an (a+b)-valent organic radical,

R$^e$ and R$^f$ are C$_1$-C$_5$-alkyl, or the two radicals, together with the C atom to which they are bonded, are a cycloalkane or alkylcycloalkane ring, or one of R$^e$ and R$^f$, together with the C atom to which it is bonded and the radical Z' or part of the radical Z' is a cycloalkane or alkylcycloalkane ring, R$^d$ is C$_1$-C$_{20}$-alkyl, C$_3$-C$_{15}$-alkoxyalkyl, C$_5$-C$_{12}$-cycloalkyl, C$_7$-C$_{13}$-aralkyl, phenyl or a radical —C$_m$H$_{2m}$—CO—V—C$_n$H$_{2n}$—B, in which m is a number from 1 to 20, n is a number from 1 to 4 and V is —O— or —N(R$^{22}$) wherein R$^{22}$ is hydrogen, C$_1$-C$_{18}$ alkyl or phenyl, or R$^d$ together with an R$^c$ in the ortho-position and the aromatic ring, is a coumaran or chroman ring, or, if a is 1, R$^d$ can also be a radical of the formula

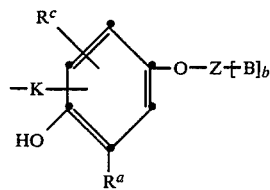

in which s is 1 or 2 and, if s is 1, L is C$_2$-C$_{12}$-alkylene, which can be interrupted by one or two O or S atoms, C$_4$-C$_{10}$-alkenylene, C$_4$-C$_6$-alkynylene, C$_5$-C$_{12}$-cycloalkylene, xylylene or a radical of the formula

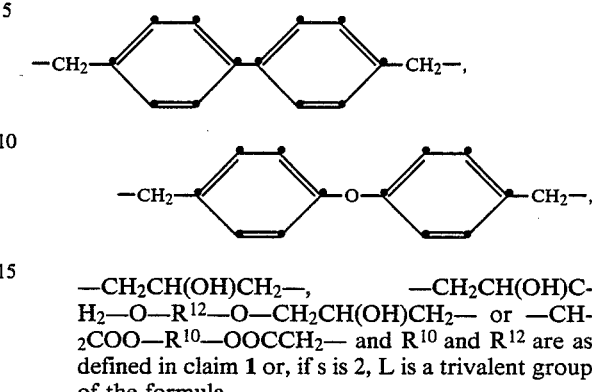

—CH$_2$CH(OH)CH$_2$—, —CH$_2$CH(OH)CH$_2$—O—R$^{12}$—O—CH$_2$CH(OH)CH$_2$— or —CH$_2$COO—R$^{10}$—OOCCH$_2$— and R$^{10}$ and R$^{12}$ are as defined in claim 1 or, if s is 2, L is a trivalent group of the formula

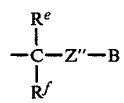

R$^a$ is a monovalent hydrocarbon radical which sterically hinders the OH group, Z is a (1+b)-valent organic linking radical, B is as defined in claim 1, R$^c$ is hydrogen or C$_1$-C$_8$-alkyl, a and b independently of one another are numbers from 1 to 3 and (a+b) is a number from 2 to 4, and R$^b$ is hydrogen or, if a is 1, can also be a radical of the formula in which R$^c$, R$^a$, Z, B and b are as defined above, K is a direct bond or a divalent group of the formula —S—, —S—S—, —SO—, —SO$_2$—, —CH$_2$SCH$_2$—, —CH$_2$OCH$_2$—, —CH(R$^{21}$)— or —N(R$^{22}$)—, in which R$^{21}$ is hydrogen, C$_1$-C$_{12}$-alkyl, or C$_3$-C$_{15}$-alkyl which is interrupted by —S— or —O— and R$^{22}$ is hydrogen, C$_1$-C$_{18}$-alkyl or phenyl, or R$^b$ is a radical of the formula $$-\underset{R^f}{\underset{|}{\overset{R^e}{\overset{|}{C}}}}-Z''-B$$

wherein R$^e$, R$^f$ and B are as defined above and Z'' is a divalent organic radical.

* * * * *